United States Patent [19]

Purcell et al.

[11] Patent Number: 4,511,556

[45] Date of Patent: Apr. 16, 1985

[54] INACTIVATION OF A LIPID VIRUS

[75] Inventors: Robert H. Purcell, Boyds, Md.; Stephen M. Feinstone, Washington, D.C.

[73] Assignee: The United States of America as represented by the Department of Health and Human Services, Washington, D.C.

[21] Appl. No.: 386,991

[22] Filed: Jun. 10, 1982

[51] Int. Cl.³ .................... A61K 35/14; A61K 39/12; A61K 31/02; C12N 7/06
[52] U.S. Cl. .................................. 514/743; 424/89; 435/238; 514/758
[58] Field of Search .................... 424/89, 101, 350; 435/238; 422/37

[56] References Cited

U.S. PATENT DOCUMENTS 4,031,204 10/1980 Davis ................................. 424/90
4,230,697 6/1977 Nishida et al. ....................... 424/177
4,302,444 11/1981 Baxendale ............................ 424/89

OTHER PUBLICATIONS

Purcell, "The Hepatitis Viruses: An Overview and Historical Perspective," *Viral Hepatitis*, 1981, Franklin Institute Press.

Maramorosch et al., *Methods in Virology*, vol. 2, 1967.

*Primary Examiner*—Robert J. Warden
*Assistant Examiner*—Shawn P. Foley
*Attorney, Agent, or Firm*—John S. Roberts, Jr.

[57] ABSTRACT

A method of inactivating a lipid virus in a protein carrier selected from the group consisting of Hepatitis B virus (HBV) and non-A, non-B hepatitis (NANBH) by contacting said virus for an extended period of time and ambient temperature with a halohydrocarbon treating agent preferably chloroform in an amount of 5% v/v to 50% v/v.

21 Claims, 1 Drawing Figure

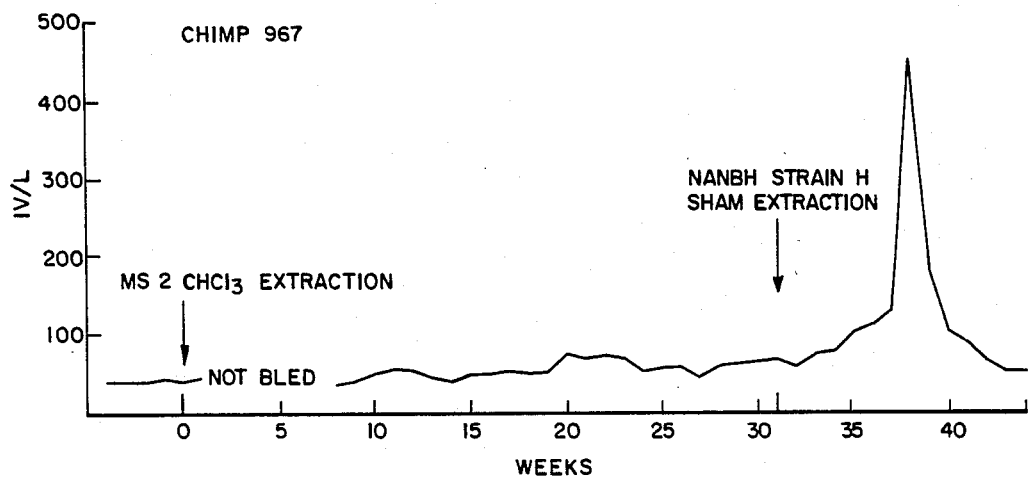
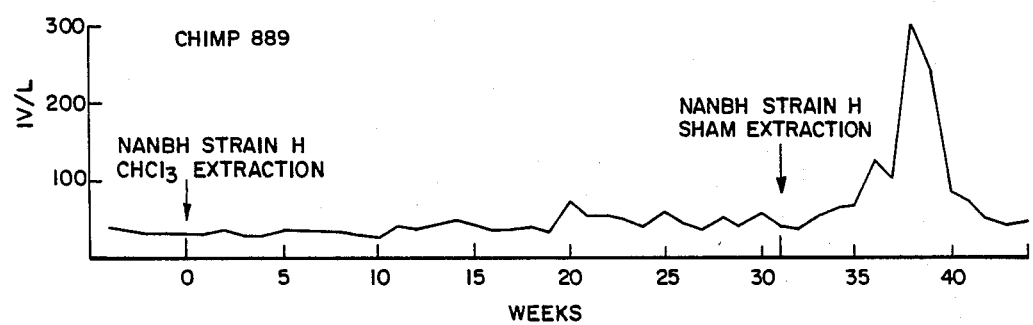
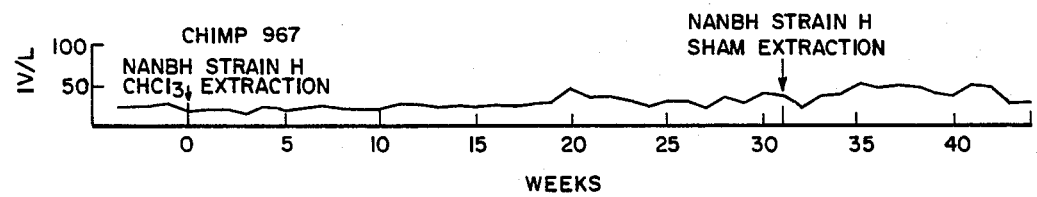

INACTIVATION OF A LIPID VIRUS

Viral hepatitis has been recognized as an important and serious sequela of parenteral exposure to blood and blood components since the early 1940s. It was originally believed that all such blood-associated hepatitis was caused by the serum hepatitis virus (now called the hepatitis B virus, or HBV). Subsequently the development of sensitive assays for infection with this virus revealed that only approximately ⅓ of transfusion-associated hepatitis was caused by the HBV. It was thought that the remaining hepatitis was caused by the hepatitis A virus. However, the development of sensitive assays for HAV led to the recognition of a new hepatitis virus, the non-A, non-B hepatitis virus (NANB) in 1975. The successful application of sensitive screening tests for HBV to blood donors has resulted in a decrease (but not disappearance) of HBV in transfusion-associated hepatitis; at present approximately 90 percent of such hepatitis is caused by non-A, non-B agents.

Similarly, hepatitis following administration of blood products such as antihemophilic factor was thought to be caused solely by HBV. However, in the late 1970s, the association of NANB agents with administration of antihemophilic factor to hemophiliacs was reported and confirmed. As the transfusion-associated hepatitis, the application of serologic screening methods to plasma donors has resulted in a relative decrease in the importance of HBV in such blood product-associated hepatitis.

Unfortunately, serologic tests for the detection of NANB agents are not available for detection of potentially infectious donors because the agents have not been adequately identified and characterized despite extensive efforts to do so. Therefore, blood plasma products remain potential sources for transmission of hepatitis agents to recipients. The resultant hepatitis can be quite serious, even life-threatening, and can result in not only acute heptatitis but also chronic hepatitis in a significant proportion of cases.

For these reasons attempts to inactivate hepatitis agents in blood plasma products have been pursued with vigor. Such approaches have included the use of heat, the addition of anti-HBV antibody, the use of solid immunoadsorbents or other chemical-specific adsorbents, exposure to ultraviolet radiation, the addition of certain inactivating substances, such as beta-propriolactone, surface-active substances, etc. None of the approaches has been entirely successful and some have introduced an added potential risk (e.g., beta-propiolactone-carbinogenic). Some of the approaches have not been tested for efficacy (e.g., surface-active substances). Failure of these approaches stems from relative resistance of the agents to physical or chemical inactivation, particularly when in the presence of high protein concentrations as occurs with blood products and from limited knowledge about the nature of the hepatitis agents, especially the NANB agents.

As part of a systematic characterization of NANB agents by standardized virologic methods, the present inventors have established that HBV and at least one NANB agent contain lipids essential for the integrity and viability of the viruses. This was established by exposing the viruses to a potent lipid solvent (chloroform) and demonstrating that such chloroform-extracted viruses were rendered noninfectious in a suitable susceptible host, the chimpanzee (*Pan troglodytes*).

It is understood that the present invention applies to all lipid containing NANBH particles which of necessity may be more than one particle as, for example, the more recently discovered delta particle.

The present invention relates to a method of inactivating a lipid virus in a protein carrier where said virus is selected from a group consisting of hepatitis B virus (HBV) and non-A, non-B hepatitis (NANBH) virus. This is achieved by contacting said virus in the carrier for an extended period of time at generally ambient temperatures with a halohydrocarbon treating agent. This treating agent is selected from a preferred chloroform, $CHCl_3$, and includes the most common Freon agents which are $CH_2F_2$, $CCl_2F_2$, and others, in an amount of 5 to 50% v/v.

The period of time noted above for treatment is about one-half to five hours and the generally ambient temperature is from about 4° C. to 40° C. The treating agent of choice is chloroform, $CHCl_3$, and it is noted that the method has been utilized both where the extraction of the aqueous blood plasma products is made by physical means, centrifugation, or otherwise, but also where the extraction is made of the lyophilized dried blood products and the removal of the solvent is made by appropriate means which includes vacuum evaporation. Generally, these two processes can be distinguished in that in the latter there is a reduction to powder form after utilization. It has been found that there is a need for protection of products which have been lyophilized.

The inactivation of HBV and NANBV has been shown in animals as with chimpanzees.

Non-A, non-B hepatitis is the major cause of transfusion associated hepatitis in the United States. Presently less than 10% of post-transfusion cases are caused by the hepatitis B virus. Of the remainder, cytomegalovirus may account for a small proportion but the vast majority are caused by an as yet unidentified agent. There is a large amount of evidence supporting a transmissable agent as the cause of NANBH. This includes transmission studies done in both humans and non-human primates. Chimpanzees and marmoset monkeys have both been shown to be susceptible to infection by at least some NANBH agents. Though very costly and cumbersome to work with, these animals can be used to aid in the characterization of the infectious agent of NANBH.

One of the fundamental characteristics of viruses is whether or not they contain essential lipid as part of their structure. Viruses that do contain essential lipid can be inactivated by lipid solvents such as ether or chloroform. This invention particularly relates to the chloroform sensitivity of the H strain of NANBH.

A list of lipid containing viruses which may be inactivated by extraction with chloroform or other lipid solvents of the present invention include members of the herpesvirus group (cytomegalovirus, Epstein-Barr virus, herpes zoster virus, herpesvirus type 1 and herpesvirus type 2), the delta agent (a type of non-A, non-B hepatitis virus), and members of other blood-borne virus groups including the togaviruses (including rubella virus) and the bunyaviruses, retroviruses (including the newly discovered human T-cell leukemia virus), orthomyxoviruses (influenza), paramyxoviruses (measles, mumps), rhabdoviruses (rabies, Marburg agent), and arenaviruses (Lassa fever, other hemorrhagic fevers) as well as other members of the poxvirus group.

It has been mentioned in the literature that diethyl ether is an effective inactivating agent for destroying endotoxin or infectivity of non-hepatitis viruses and preventing clotting activation. However, it is a less efficient solvent of lipids. Also, the use of diethyl ether is not recommended for the broader use of the present agents in the nuclization of pox virus; such pox virus may be illustrated by smallpox and vaccinia virus. Not only is diethyl ether noted but other ethers, such as phenoxy, polyethoxy ethanol, and compounds of the general formula $RC_6H_4(OC_2H_4)_nOH$ are also noted.

The present use of chloroform and the Freon or Genetron fluorocarbon agents has been found useful in so-called lipid viruses which include HBV and NANBH and also include those virus particles which have a lipid outer coat which is susceptible to removal by treatment.

In the utilization of this invention, chloroform, is preferred, but as alternative reagents which are operable there can be used a Freon which is defined as a chlorofluoro carbon of one or two carbon atoms. These may be viewed as fluorinated derivatives of methane and ethane. Additionally, there may be utilized as Freons chlorofluoro carbons as, for example, $CCl_3F$, $CCl_2F_2$, $CCL_2FCClF_2$, etc. For example, in the methane and ethane series, according to the current numbering, the following compounds are operable: $CCl_3F$, $CCl_2F_2$, $CHClF_2$, $CCl_2F$—$CClF_2$, and $CClF_2$—$CClF_2$ and numbered 11, 12, 22, 113, and 114, respectively.

STATEMENT OF PRIOR ART

A review of the prior art of patents is as follows:

U.S. Pat. No. 4,113,712 Funakoshi—Utilization of a surfactant such as the Tritons or Tweens for hepatitis B surface antigen particles.

U.S. Pat. No. 4,139,630 Asculai et al—Utilization of non-ionic surfactants as inactivating agents for herpes simplex virus.

U.S. Pat. No. 4,314,997 Shanbrom—A non-denaturing amphiphile used to inactivate hepatitis viruses B and non-A, non-B in amount of 0.25-10% by weight and citing non-ionic, anionic, and cationic surfactants.

U.S. Pat. No. 4,315,919 Shanbrom—Similar disclosure to 4,314,997 above.

Purcell, "The Hepatitis Viruses: An Overview and Historical Perspective, " *Viral Hepatitis,* 1981 International Symposium, ed. Szmuness, Alter and Maynard, Franklin Institute Press, Philadelphia, pp. 3–12.

Philipson, "Water-Organic Solvent Phase Systems," *Methods in Virology,* ed. Maramorosch et al, Volume II, 1967, pp. 235–244.

DESCRIPTION OF THE DRAWING

The FIGURE shows a plot according to time on the ordinate of the chimpanzee treatment with chloroform extracted non-A, non-B virus and hepatitis B virus, and at the conclusion of the test there were negative 31 weeks after inoculation. Additional sham tests were made where there was no chloroform inactivation of the virus and the animals got hepatitis.

EXAMPLE 1

Infectious Inoculum

Human plasma, designated H, was drawn by plasmaphoresis from a patient with acute post-transfusion NANBH. A portion of the plasma unit had previously been aliquoted into 1 ml vials and a tenfold dilution series in fetal calf serum from $10^0$ to $10^{-10}$ was prepared, aliquoted into 1 ml quantities in vials and stored at $-70°$ C. until use. This plasma had been shown to have a chimpanzee infectivity titer of at least $10^6$. One ml of this plasma at a $10^{-1}$ dilution was thawed and treated as described below.

A human hepatitis B serum designated MS-2 containing $10^8$ chimpanzee infectious doses per ml had also previously been aliquoted, diluted and stored in a similar way to the NANBH plasma. A one-ml vial of a $10^{-3}$ dilution of the MS-2 serum was thawed and treated as described below.

Control Viruses

Representative chloroform sensitive and resistant viruses were selected as internal and external controls. The internal controls were added directly to the NANBH plasma or to the HBV serum. The internal control viruses were selected because the human serum or plasma containing the hepatitis agents lacked antibody to the control viruses, they would not replicate significantly in chimpanzees which were to be used to assay the hepatitis viruses, and they would be separately assayed each in the presence of the other without interference. Avian influenza virus H.N. was used as the chloroform sensitive internal control. Approximately $10^8$ $TCID_{50}$ was added to each of the hepatitis specimens. The coliphage $\phi \times 174$ was used as the chloroform resistant virus and approximately $10^9$ infectious particles were added to each of the hepatitis specimens. External control viruses were chosen because they represented typical human infectious agents and could be easily assayed. One ml of poliovirus type I LSC vaccine stain containing approximately $10^7$ $TCID_{50}/ml$ added to one ml of a 1:10 dilution of fetal calf serum which was then diluted to a final volume of 10 ml served as the chloroform resistant external control virus. One ml of Vaccinia virus Elstree strain containing approximately $10^6$ $TCID_{50}$ was added in a similar way to fetal calf serum and served as the chloroform sensitive external control virus.

Chloroform extraction

Each hepatitis and each external control fetal calf serum preparation was diluted to a final volume of 10 ml or a 1:100 final concentration of serum or plasma. Each 10 ml specimen was then equally aliquoted into two glass screw-cap tubes. To one of the tubes of each specimen, 0.55 ml of chloroform from a freshly opened bottle was added to make a final 10% (v/v) chloroform concentration. All tubes (both those containing and not containing chloroform) were then agitated on a vortex mixer for 10 minutes at room temperature and centrifuged at 1000 RPM for 10 minutes in a Sorvail 3B centrifuge.

The aqueous phase was then carefully pippeted off the interface of the chloroform containing samples and off any pelleted solid material from the samples not containing chloroform. These were aliquoted into 1 ml amounts and stored at $-70°$ C. until assayed.

Viral infectivity assays

Avian influenza virus was assayed on MDCK cells by CPE and hemadsorption with guinea pig red blood cells. Quadruplicate wells of six well plates were inoculated for each dilution of a serial 10-fold dilution series of both the chloroform-treated and sham-treated specimen.

φ×174 was assayed by tube dilution (quadruplicate samples) in L broth of each sample to be tested using *E. coli* 4704 as the host cell.

Vaccinia virus infectivity was assayed by CPE in Vero cells. Quadruplicate wells of 6 well plates were inoculated with serial 10-fold dilutions of the fetal calf serum suspensions containing Vaccinia virus and the relative titers of the chloroform-treated and the sham-treated specimens were compared.

Poliovirus was assayed by CPE in Vero cells in the same manner as the Vaccinia virus.

Chimpanzee inoculations

Two chimpanzees were inoculated with one ml each of the chloroform-treated H plasma. One chimpanzee was inoculated with one ml of the chloroform-treated MS-2 serum. The chimpanzees were monitored for hepatitis by determination of alanine amino transferase (ALT) levels and aspartate amino transferase (AST) levels on weekly plasmapheresis samples. Hepatitis B surface antigen (HBsAg), antibody to HBsAg (anti-HBs) and antibody to hepatitis B core antigen (anti-HBc) were also measured in the plasma from the MS-2 inoculated chimpanzee using commercial radioimmunoassays (Ausria, Ausab and Corab, Abbott Laboratories). In addition, percutaneous liver biopsies were obtained weekly from all chimpanzees. These biopsies were divided into three pieces and fixed in 10% buffered formalin for routine histology, glutaraldehyde for electron microscopy and snap frozen for immunofluorescence.

Diagnosis of hepatitis

Hepatitis was diagnosed in a chimpanzee if the ALT level rose to more than twice the upper limit of normal considered to be forty IU/L. Hepatitis was confirmed by light and electron microscopy on the liver biopsies.

RESULTS

All the internal and external control viruses reacted to the chloroform treatment as predicted and these results are summarized in Table 1. The avian influenza virus and Vaccinia virus were totally inactivated by chloroform while poliovirus and φ×174 were essentially unaffected.

TABLE 1

Chloroform Extraction of Control Viruses

| | Virus Titer $Log_{10}$ $ID_{50}/0.1$ ml | |
|---|---|---|
| | $CHCl_3$ Extraction | Sham Extraction** |
| Internal Controls | | |
| ox 174 in H Plasma* | 9.0 | 9.5 |
| MS-2 Serum*/Fetal Calf Serum* | 9.0 | 9.5 |
| Avian Influenza | | |
| Virus in H Plasma* | ≦0.5 | 5.25 |
| MS-2 Serum/Fetal Calf Serum* | ≦0.5 | 5.5 |
| External Controls | | |
| Polio Virus Type 1 in Fetal Calf Serum* | 6.5 | 6.5 |
| Vaccinia Virus in Fetal Calf Serum* | ≦0.5 | 5.5 |

*Final total serum or plasma concentration was 1:100 for each virus suspension.
**Without $CHCl_3$ The FIGURE shows the weekly ALT levels in the two chimpanzees (nos. 889 and 947) inoculated with the chloroform-treated H plasma and the one chimpanzee (no. 967) inoculated with the chloroform-treated MS-2 serum. As can be seen, none of these animals developed biochemical evidence of hepatitis. Chimpanzee 967 that was inoculated with the MS-2 plasma did develop anti-HBs but not anti-HBc which is a typical hepatitis B vaccine response indicating HBsAg was in the inoculum but not infectious virus. This animal was probably resistant to infection with live HBV due to its acquisition of antiHBs. Therefore, it was not challenged with the sham-treated MS-2 plasma. Six months after the initial inoculation, all three of these animals were inoculated with the sham-treated H plasma. As can be seen in the FIGURE, chimpanzee 967 that had no prior exposure to NANBH developed NANBH with a 5-week incubation period. Chimpanzee 889 that had initially been inoculated with the chloroform-treated H plasma also developed NANBH with an incubation period of about 5 weeks after rechallenge with the sham-treated H plasma. However, chimpanzee 947 showed no evidence of hepatitis following either inoculations with the chloroform-treated or shamtreated H plasma.

In a preliminary, uncontrolled experiment, a $10^{-2}$ dilution of the H plasma was still infectious in a chimpanzee after treatment with 5% v/v chloroform. However, this animal has an incubation period of 9.5 weeks, indicating that the virus titer was reduced by the chloroform treatment.

Two human plasma samples in chimpanzees have been studied and one was found to have an infectivity titer of less than $10^2$. The other, however, infected a chimpanzee at a $10^{-6}$ dilution. This relatively high-titered plasma makes certain characterization experiments possible that cannot be done properly with a low-titered inoculum. In this experiment the starting plasma was diluted to a final $10^{-2}$ dilution in order to remove most of the effect of the high concentrations of plasma on the chloroform extraction and still allowed a test to see if $10^4$ chimpanzee infectious units could be inactivated by chloroform. All other chimpanzee inocula that have been reported have a relatively low titer, usually $10^3$ or below. These inocula have much less utility for many characterization experiments.

Hepatitis B virus does not contain a lipid envelope derived from a cell membrane but the coat is composed of lipoprotein. $10^4$ infectious doses of HBV were completely inactivated by treatment with chloroform. Since $10^4$ chimpanzee infectious doses of the H strain of NANB were also inactivated by chloroform, then it was concluded that this agent also contained essential lipid.

EXAMPLE 2

Chloroform Inactivation of Test Viruses in Antihemophilic Fraction

This experiment was performed to determine if chloroform extraction of lyophilized antihemophilic fraction efficiently inactivated 2 lipid-containing viruses, an influenza virus and a pox virus.

Inactivation of these viruses by chloroform extraction of aqueous samples is a standardized procedure. Such chloroform extraction has been employed to inactivate hepatitis B virus and non-A, non-B hepatitis virus in diluted plasma samples. However, a practical application of this procedure to inactivation of hepatitis viruses in commercial antihemophilic fraction could require extraction of the dry powder. The purpose of this protocol was to confirm that such inactivation takes place with "standard" viruses. Avian influenza virus was used because humans lack antibody to this virus. Although the general population has antibody to vaccinia virus, this virus was used with appropriate controls to determine whether traces of antibody in the antihemophilic fraction neutralized the virus.

Commercial AHF was inoculated with a measured amount of avian influenza virus (A/S8) or vaccinia virus (ATCC VR 862 Lot 1) or tissue culture medium (MEM complete with 10% FBS). The product was lyophilized and extracted with chloroform at 1 of 3 temperatures: 5°, 20° or 40° C. The chloroform-extracted and control samples were reconstituted with water for injection and the infectivity titers of influenza virus and vaccinia virus determined in appropriate tissue culture systems.

The tissue culture infectious dose 50 titer of the avian influenza pool was $10^{7.5}$/ml; the vaccinia virus pool was approximately $10^{6.5}$/ml. Three 30 ml vials of AHF from the same lot were reconstituted with 30 ml of water for injection. To vial #1 was added 1 ml of avian influenza virus inoculum. To vial #2 was added 1 ml of vaccinia virus inoculum. To vial #3 was added 1 ml of tissue culture medium. Each vial was thoroughly mixed (without foaming). 5 ml of each vial was distributed into 6 companion vials, labeled respectively 1A, 1B, 1C, 1D, 1E, 1F, 2A, 2B, 2C, 2D, 2E, 2F, etc. (see Table 1). All 18 vials were lyophilized and sealed. Vials A, B, and C were extracted with chloroform as per the table; vials D, E and F were held at 5°, 20° and 40°, respectively, in the lyophilized state as controls. After chloroform extraction vials 1A through F and vials 2A through F were returned to the Hepatitis Viruses Section for performance of infectivity titrations. The vials were maintained at 5° C. or lower temperature during transit and storage.

Calculation:

Av. flu pool ($TCID_{50}$ of $10^{7.5}$) diluted $10^{-1.5}=10^6$ $TCID_{50}$/ml.

Vaccinia pool ($TCID_{50}$ of $10^{6.5}$) diluted $10^{-1.5}=10^5$ $TCID_{50}$/ml.

EXAMPLE 3

Chloroform extraction of lyophilized Factorate

Lyophilized Factor VIII (Factorate-Armour) was extracted with chloroform using three different procedures.

A. 1 gram of Factorate (dry powder) was mixed at 4° C. for 20 minutes with 20 ml of cold chloroform. The chloroform was then removed by filtration and the dry powder was washed on the filter with an additional 10 ml of cold chloroform.

B. 1 gram of Factorate (dry powder) was mixed with 10 ml of cold chloroform at 4° C. for 10 minutes. The chloroform was removed by filtration and the powder was washed on the filter with 5 ml of cold chloroform. This process was then repeated a second time.

C. 1 gram of Factorate (dry powder) was mixed with 20 ml of chloroform at room temperature for 20 minutes. The chloroform was removed by filtration and the dry powder was washed on the filter with 10 ml of chloroform at room temperature.

The samples were reconstituted with deionized water and assayed for Factor VIII:c, Fibronectin, and Fibrinogen (Table 2).

TABLE 2

Factor VIII, Fibronectin and Fibrinogen Activity of Lyophilized Factorate after Chloroform Extraction

| Sample | Factor VIIIc Units/ml | Fibronectin mg/ml | Fibrinogen mg/ml |
|---|---|---|---|
| Control | 9.1 | 1.11 mg | 8.9 mg |
| Room Temp. Extraction | 9.5 | 1.14 mg | 9.3 mg |
| 4° C. 1 × Extracted | 8.9 | 1.19 mg | 9.3 mg |
| 4° C. 2 × Extracted | 9.3 | 1.29 mg | 8.6 mg |

We claim:

1. A method of inactivating viruses that contain essential lipids in a blood plasma product which comprises contacting said product with at least one halohydrocarbon treating agent selected from the group consisting of chloroform and a freon and removing said treating agent.

2. The method of claim 1 wherein the blood plasma product is dry powder.

3. The method of claim 1 wherein the treating agent is chloroform.

4. A blood plasma product produced by the method of claim 1.

5. The method of claim 1 wherein the blood plasma product is liquid.

6. The method of claim 1 wherein the treating agent is a freon.

7. The method of claim 1 wherein the virus is a hepatitis virus selected from hepatitus B virus and non-A, non-B hepatitis virus.

8. The method of claim 7 wherein the virus is hepatitis B virus.

9. The method of claim 7 wherein the virus is non-A, non-B hepatitis virus.

10. The method of claim 1 wherein the treating agent is removed by phase separation.

11. The method of claim 1 wherein the treating agent is removed by evaporation.

12. The method of claim 1 wherein the biological potency of the blood plasma product is preserved.

13. A method of inactivating viruses that contain essential lipids in a blood plasma product which comprises contacting said product with at least one halohydrocarbon treating agent selected from the group consisting of chloroform and a freon for about one-half to five hours at a temperature of about 4°-40° C. and at about 5-50% v/v and removing said treating agent.

14. The method of claim 13 wherein the treating agent is chloroform.

15. The method of claim 13 wherein the treating agent is a freon.

16. The method of claim 13 wherein the virus is a hepatitis virus selected from hepatitis B virus and non-A, non-B hepatitis virus.

17. The method of claim 16 wherein the virus is hepatitis B virus.

18. The method of claim 16 wherein the virus is non-A, non-B hepatitis virus.

19. The method of claim 13 wherein the treating agent is removed by phase separation.

20. The method of claim 13 wherein the treating agent is removed by evaporation.

21. The method of claim 13 wherein the biological potency of the blood plasma product is preserved.

* * * * *